US Patent Number: 4,931,385
Date of Patent: Jun. 5, 1990

Inventors: Elliott Block, Wellesley Hills; Izak Bahar, Chestnut Hill; Frank Cole, Stow; Cheryl A. Eaton, Southboro; Wendy Jones, Burlington; Eric Sigillo, Lawrence; Mary Coseo, Arlington; Nancy J. Cicia, Wakefield; L. Edward Cannon, Wayland; Walter Cantarow, Norwood, all of Mass.

Assignee: Hygeia Sciences, Incorporated, Newton, Mass.

Appl. No.: 275,656

Filed: Nov. 21, 1988

[54] ENZYME IMMUNOASSAYS AND IMMUNOLOGIC REAGENTS

Related U.S. Application Data

[63] Continuation of Ser. No. 747,605, Jun. 24, 1985, abandoned, which is a continuation-in-part of Ser. No. 473,907, Mar. 10, 1983, abandoned.

[51] Int. Cl.$^5$ .............. G01N 33/535; G01N 33/543; C12N 9/96; C12Q 1/28
[52] U.S. Cl. .............. 435/7; 435/28; 435/188; 435/810; 435/805; 436/518; 436/814; 436/818; 436/808; 436/810; 436/826
[58] Field of Search .............. 435/4, 7, 28, 188, 810; 436/507, 513, 548, 518, 531, 814, 818, 808, 810, 826

[56] References Cited

U.S. PATENT DOCUMENTS

| | | | |
|---|---|---|---|
| 2,908,614 | 10/1959 | Muggleton et al. | 167/78 |
| 3,378,443 | 4/1968 | Cooper et al. | 167/78 |
| 3,423,290 | 1/1969 | Seamans, Jr. et al. | 195/99 |
| 3,579,306 | 5/1971 | Crane | 23/253 |
| 3,654,090 | 4/1972 | Schuurs et al. | 435/7 |
| 3,791,932 | 2/1974 | Schuurs et al. | 195/103.5 |
| 3,825,410 | 7/1974 | Bagshawe | 23/230 R |
| 3,860,484 | 1/1975 | O'Malley | 435/188 |
| 3,880,714 | 4/1976 | Babson | 195/99 |
| 3,963,441 | 6/1976 | Dietrich | 23/253 R |
| 3,987,159 | 10/1976 | Spona et al. | 424/12 |
| 4,017,597 | 4/1977 | Reynolds | 424/1.5 |
| 4,062,933 | 12/1977 | Wolfangel | 424/1 |
| 4,094,647 | 6/1978 | Deutsch et al. | 23/253 TP |
| 4,115,535 | 9/1978 | Giaever | 424/1 |
| 4,157,280 | 6/1979 | Halpert et al. | 195/127 |
| 4,169,012 | 9/1979 | Dawson et al. | 435/7 |
| 4,188,371 | 2/1980 | Weetall | 424/1 |
| 4,200,690 | 4/1980 | Root et al. | 435/7 |
| 4,206,200 | 6/1980 | Guthohrlein et al. | 424/92 |
| 4,228,240 | 10/1980 | Dawson et al. | 435/7 X |
| 4,248,965 | 2/1981 | Mochida et al. | 435/7 |
| 4,256,833 | 3/1981 | Ali et al. | 435/7 |
| 4,273,868 | 6/1981 | Walter | 435/14 |
| 4,280,816 | 7/1981 | Elahi | 23/230 |
| 4,287,300 | 9/1981 | Gibbons et al. | 435/5 |
| 4,299,916 | 11/1981 | Litman et al. | 435/6 |
| 4,310,504 | 1/1982 | Derfler et al. | 424/1 |
| 4,340,395 | 7/1982 | Magers et al. | 23/230 B |

(List continued on next page.)

FOREIGN PATENT DOCUMENTS

| | | | |
|---|---|---|---|
| 42755 | 12/1981 | European Pat. Off. | |
| 2712044 | 9/1977 | Fed. Rep. of Germany | |
| 2804920 | 5/1979 | Fed. Rep. of Germany | |
| 2805003 | 5/1979 | Fed. Rep. of Germany | |
| 2388275 | 11/1978 | France | |
| 147368 | 4/1981 | German Democratic Rep. | 435/192 |
| 56-27654 | 3/1981 | Japan | |
| 188067 | 9/1985 | Japan | 435/188 |
| 8001972 | 11/1981 | Netherlands | |
| 2049700 | 12/1980 | United Kingdom | |
| 2062224 | 5/1981 | United Kingdom | |

OTHER PUBLICATIONS

Decker (1980) Chem. Abstr 92:39735t.
P. Nakane, "Preparation and Standardization of Enzyme-Labeled Conjugates", *Immunoassays in the Clinical Laboratory*, Alan R. Liss, Inc., pp. 81–87 (1979).
E. Engvall, "Immunochemical techniques", in *Methods in Enzymology*, Part A, H. V. Vunakis et al., eds. Academic Press, New York, pp. 430–432 (1980).
P. K. Nakane et al., "Peroxidase-Labeled Antibody A New Method of Conjugation", *J. of Histochemistry and Cytochemistry*, vol. 22, pp. 1084–1091 (1974).
M. Uotila et al., "Two-Site Sandwich Enzyme Immunoassay with Monoclonal Antibodies to Human Alpha Fetoprotein", *J. Immunological Methods* 42, pp. 11–15 (1981).

Primary Examiner—Esther M. Kepplinger
Attorney, Agent, or Firm—John P. Kirby, Jr.; Margaret A. Pierri; Barry D. Josephs

[57] ABSTRACT

Detection of bindable substances such as antibodies and antigens using enzyme linked immunosorbent assays having particular utility in home diagnostic applications. The preferred implementation of the invention is characterized by the steps of admixing a sample suspected of containing the bindable substance to be detected with an antibody-enzyme conjugate, immersing an antibody coated solid support into the mixture and then exposing the coated support to an activated chromogenic solution. The conjugate for use in the home diagnostic assay is preferably contained within a lyophilized mixture. The lyophilized mixture contains components which preserve the antibody-conjugate's reactivity and immunologic binding specificity even if the lyophilized mixture had been subjected to hot, humid environmental conditions. Active components in the lyophilized mixture include polyethylene glycol, sugars, and surfactant. The antibody coated support is treated with an improved blocking solution containing a blocking agent such as bovine serum albumin or milk protein in admixture with a sugar. The blocking solution prevents nonspecific binding of immunologic reagents to the support and protects the antibody on the support from loss of reactivity and immunologic binding specificity even if the antibody coated support had been subjected to hot, humid environmental conditions.

15 Claims, No Drawings

U.S. PATENT DOCUMENTS

| | | | |
|---|---|---|---|
| 4,343,896 | 8/1982 | Wolters et al. | 435/7 |
| 4,376,110 | 3/1983 | David et al. | 435/7 X |
| 4,385,114 | 5/1983 | Guthlein et al. | 435/28 |
| 4,386,224 | 5/1983 | Deetman | 568/703 |
| 4,391,904 | 7/1983 | Litman et al. | 435/7 |
| 4,444,879 | 4/1984 | Foster et al. | 435/7 |
| 4,446,232 | 5/1984 | Liotta | 435/7 |
| 4,448,882 | 5/1984 | Brodbeck et al. | 435/188 |
| 4,457,916 | 7/1984 | Hayashi et al. | 424/101 |
| 4,458,014 | 7/1984 | Ebersole | 435/7 |
| 4,459,358 | 7/1984 | Berke | 436/170 |
| 4,459,359 | 7/1984 | Neurath | 436/507 |
| 4,486,530 | 12/1984 | David et al. | 435/7 |
| 4,503,143 | 3/1985 | Gerber et al. | 435/7 |
| 4,517,290 | 5/1985 | Iwasa et al. | 435/7 |
| 4,525,452 | 6/1985 | Jones et al. | 435/7 |
| 4,615,972 | 10/1986 | Gallacher | 435/28 |
| 4,659,666 | 4/1987 | May et al. | 435/188 |
| 4,681,782 | 7/1987 | Ozkan | 428/36 |

ENZYME IMMUNOASSAYS AND IMMUNOLOGIC REAGENTS

BACKGROUND OF THE INVENTION

This is a continuation of application Ser. No. 747,605, filed June 24, 1985, now abandoned, entitled "IMPROVED ENZYME IMMUNOASSAYS AND IMMUNOLOGIC REAGENTS", which was a Continuation in Part of Application Ser. No. 473,907 filed Mar. 10, 1983 now abandoned.

1. Field of the Invention

The present invention relates to enzyme immunoassay techniques for the detection of bindable substances, such as antibodies and antigens, of particular utility in home diagnostic kits. The invention further relates to simplified, reliable procedures for such immunoassays.

2. Description of the Prior Art

There are a number of immunoassay techniques in contemporary use for laboratory detection and measurement of antigens or antibodies present within a test sample. Most of these techniques, however, are unsuitable for use outside a laboratory setting because of complexity of the detection equipment and other difficulties inherent in conducting many conventional immunoassay techniques. Thus, there is a need for a technique suited for home diagnostic immunoassay kits which may be readily used, for example, for the detection of antigens such as human chorionic gonadotropin hormone (hCG, antigen) which is present in the urine of pregnant women. In order for a diagnostic immunoassay kit to be satisfactory for use in the home or physician's office, the kit should be relatively inexpensive, and the immunoassay method must be easy to use, reliable, efficient, and above all must be safe. Additionally, the test method must be of sufficient sensitivity to easily detect the desired antigen in the test sample.

The conventional immunoassay methods for detection and measurement of antigens or antibodies in a test sample are the radioimmunoassay method (RIA) and the fluorescence immunoassay technique (FIA). The radioimmunoassay technique requires the handling of radioactive materials using expensive detection equipment. These methods are therefore unsuitable for home detection kits. Immunofluorescence methods depend on expensive equipment to detect fluorescence, and present great difficulty in quantifying the test sample, rendering such methods unsuitable for home diagnostic applications.

In recent years, the enzyme immunoassay method has received increasing attention for use in detecting and measuring antibodies or antigen in test samples. The enzyme immunoassay methods involve enzyme labeling of the test antigen or antibody either directly or indirectly by labeling immune complexes which bind specifically to the test antigen or antibody. The enzyme-containing immune complexes catalyze reaction with a substrate and some means is provided for monitoring enzyme activity. One particularly well known type of enzyme immunoassay is the "ELISA", or "enzyme linked immunosorbent assay". The ELISA technique is characterized by the adsorption of the assay reactants onto a solid support, which provides an easily implemented procedure for separating the assay reactants between free and insolubilized components. A standard protocol in such assays is the repeated procedure of supplying assay materials to the solid support medium or media, incubating, and washing the solid support to remove those materials not firmly bound to the surface.

A particular ELISA technique to which the present invention relates is the "antibody sandwich" assay. In this technique, antibodies specific to the test antigen are first adsorbed in excess amount onto a solid surface such as a plastic well or tube. The test solution containing antigen is then added; the antigen will bind to the adsorbed antibody. Further steps are directed toward quantifying the bound antigen. An enzyme labeled second antibody is added and reacts with specific determinant sites on the bound antigen. The enzyme labeled second antibody is added in excess to assure that all the antigen present in the solid phase that is bound to the first antibody will also be bound to enzyme labeled second antibody. The enzyme labeled second antibody molecules will bind in a fixed ratio to each antigen molecule depending on the valence, i.e. specific available binding sites, of the antigen for the second antibody. The solid phase is then washed to remove excess second antibody and any other unbound constituents. An enzyme substrate is then added in solution in excess amount, whereby it makes contact with the bound solid phase. In colorimetric assays, the substrate includes a chromogenic material so that color development of the solid phase indicates the presence of enzyme and hence antigen.

U.S. Pat. No. 4,376,110 and M. Uotila et al., *J. of Immunological Methods*, Vol. 42 (1981) pp. 11-15, disclose the use of monoclonal antibodies in the antibody sandwich enzyme immunoassay employing one incubation. For example, U.S. Pat. No. 4,376,110 discloses the conduct of the assay by first admixing the sample suspected of containing the target antigen together with an enzyme labeled antibody conjugate and then immersing an antibody coated solid support into this mixture and incubating the coated solid support therein for a specified duration.

Although the sandwich assay of this type has been performed in laboratory settings wherein immunologic reagents may be kept refrigerated prior to use and incubations accomplished at precise temperatures, the reduction of such an assay protocol for home diagnostic implementation has heretofore presented a number of very difficult obstacles. Antibodies will lose their binding specificity and reactivity if subjected to hot or humid environmental conditions. Therefore, if the assay components are to be supplied in a kit for home use, a way must be found to preserve the reactivity and binding specificity of the antibody coated on the solid support.

Similarly, the labeled antibody conjugate is equally sensitive to adverse climactic conditions and the binding properties of the conjugate must be preserved even if the conjugate is exposed to hot, humid environmental conditions, for example, during transit or storage.

Also, for the home diagnostic application to be practical, all incubations must be satisfactorily carried out under a broad range of ambient room temperature conditions, since the home user does not have the resources for effecting precise temperature regulation during conduct of the assay. This poses another obstacle since it is known that the natural binding properties and binding reactivity of mammalian antibodies rapidly diminish as soon as the antibodies are exposed to environmental temperature conditions below 37° C. which is normal body temperature. On the other hand, typical ambient room temperature is much less than 37° C., typically in a range between 15° C. to 28° C. Another problem to be overcome in reducing the assay for home diagnostic application is to allow the user to wash the immunosorbent material, i.e. remove unbound material from the coated solid support by washing with tap water. Prior art assays typically require washing with an aqueous solution containing detergent active agent. This necessitates the inclusion of a separate vial containing the detergent solution as an additional component of the diagnostic kit.

The elimination of the detergent vial from the kit by incorporating the detergent in admixture with the labeled conjugate poses another difficult problem, however, in that detergent active components generally have a deleterious effect on the binding properties of the conjugate.

Thus, in view of all these difficulties, it must be recognized that reduction of ELISA immunoassays or more particularly the ELISA antibody sandwich assay to home diagnostic application poses a number of very difficult problems all of which must be resolved before a practical home diagnostic assay can be realized.

U.S. Pat. No. 4,228,240 describes the stabilization of peroxidase containing compositions for use in enzyme immunoassay tests. The reference recites that it is known that peroxidase whether or not coupled to another component is not very stable particularly in low concentrations and that their keeping properties are therefore poor. In immunoassays where peroxidase is typically coupled to an immunological component, it is preferable to provide the peroxidase containing composition in a lyophilized state. However, lyophilization (freeze drying) of peroxidase diminishes its activity. The reference discloses the addition of polyvalent metal ions to an aqueous solution containing peroxidase to stabilize the peroxidase and thus preserve its activity even during freeze drying. The reference discloses the addition of a sequestering agent such as ethylene diamine tetra-acetic acid (EDTA) to the solution. The reference further discloses use of metal ions to further stabilize the peroxidase. (Col. 2, lines 38–47). The reference discloses the possible addition of other components such as buffers, sugars, for example sucrose, sorbitol or mannitol, a polyethylene glycol and/or proteins, such as albumin which may also be included prior to lyophilizing the aqueous peroxidase containing composition. (Col. 2, lines 48–52).

Accordingly it is a principal object of the invention to provide an improved enzyme immunosorbent assay for detecting bindable analyte. A related objective is to provide an improved enzyme immunosorbent assay for home diagnostic application.

Another important objective is to provide a method of preserving the binding reactivity and specificity of the immunologic reagents used in the assay even if exposed to hot, humid environmental conditions. A related objective is to preserve the reactivity and binding specificity of the immunologic reagent so that all incubations may be accomplished under a broad range of ambient room temperature conditions.

Another objective is to provide a lyophilized mixture containing an antibody-enzyme conjugate with additives to preserve the binding reactivity and specificity of the conjugate over a broad range of ambient temperature and humidity conditions.

Another object is to provide an improved blocking solution for the antibody coated solid support employed in the assay.

Another object is to provide an assay wherein all washing are accomplished using ordinary tap water.

Another object is to provide an immunodiagnostic kit having the necessary components for conduct of the assay in a home environment.

SUMMARY OF THE INVENTION

In accomplishing the foregoing and related objects, the invention provides simplified, efficient enzyme immunoassay techniques for the detection of antigens and antibodies, particularly assays of the ELISA type. The assays of the preferred embodiment use the antibody sandwich method, in which a first antibody is coated onto a solid carrier, which is then incubated with a liquid mixture including an antigen test solution and enzyme-second antibody conjugate to allow immunologic reaction of the components, and selectively adsorb the reagents onto the solid phase. In the assays of the present invention, there is no separation of solid and liquid phases between adding the antigen and the conjugate. In the preferred, colorimetric detection technique, a chromogenic substrate is supplied as a final step to provide an indication of enzyme activity.

In a general description of the "simultaneous" assays of the invention, a first antibody is adsorbed onto the solid support; the test solution suspected to contain a bindable analyte is incubated therewith essentially simultaneously with the conjugate of an enzyme and a second antibody; the solid and solution phases are separated; and a substrate is added to test for the presence of enzyme in the solid phase. It is preferable to first admix the test solution with the conjugate and essentially immediately thereafter immerse the antibody coated support therein and incubate the mixture for a prescribed period under ambient room temperature conditions between about 15° C. to less than 37° C. and subsequently washing the solid phase material bound to the solid support. Typically the analyte is an antigen. Both first and second antibodies of the present assay of the invention may be polyclonals. Preferably, however, at least one of the first and second antibodies is a monoclonal; preferably both of these antibodies are monoclonals specific for the antigen. In the preferred, colorimetric technique, a chromogenic substrate is utilized to provide a visual indication of enzyme concentration or the amount of bound components may be measured by measuring the enzyme concentration as a function of the rate of reaction of the chromogenic substrate. It is a particularly advantageous aspect of the present invention that by reducing the number of elusions of the solid support there is a lessened tendency toward desorption of assay reagents.

In accordance with one aspect of the invention, the expedited assay procedures have been found particularly suitable for home and clinical diagnostic applications, which are implementable by unskilled users and require no specialized equipment. As compared with the assays of the prior art, the invention achieves time savings and utilizes simplified procedures, with fewer incubations and washing steps. The assays are suitably conducted using room temperature incubations, advantageously in the range 15° C. to less than 37° C., more preferably 15° C.–28° C. The preferred, colorimetric technique provides a definitive test for the bindable substance of interest, by giving a visual indicator having a clear delineation between positive and negative results. The assays achieve the further advantages of being reliable, safe, and cost-efficient. The preferred, double antibody sandwich technique has been found well suited to the diagnosis of a variety of antigens such as human chorionic gonadotropin hormone (hCG), gonococcus bacteria (GC), and human leutinizing hormone (hLH).

It is an important objective of the present invention to provide an enzyme immunoassay which can be applied in a home diagnostic kit.

In keeping with this objective, one important aspect of the invention assures that all immunologic reagents employed in the assay have the property that their reactivity, immunologic binding specificity and avidity are essentially completely preserved even though these immunologic reagents to be included as kit components may be exposed to hot, humid environmental conditions during transit, or prior to use in the assay. In particular, one aspect of the invention provides as one of the kit components a lyophilized product mixture which contains therein an antibody—enzyme conjugate, one of the active immunologic reagents to be utilized in the assay. The lyophilized product mixture also contains therein additives which are first blended in lyophilization solution together in admixture with the conjugate. The lyophilization solution containing conjugate and additives is subjected to freeze drying forming a powdered lyophilized (freeze dried) product. The effect of the lyophilized product mixture of the invention containing antibody-enzyme conjugate is multifold. The additives included in admixture with the conjugate in the lyophilized product have been determined to preserve the reactivity, binding specificity and avidity of the conjugate when applied to the assay even if the lyophilized product containing conjugate is subjected to hot environmental conditions between 80° F. to 120° F. In practical terms this means that the conjugate can be included in the diagnostic kit without concern that its reactivity or immunologic binding specificity will be lost if the kit components are exposed to hot, humid environmental conditions. Additionally, the user may feel free to store the lyophilized product containing conjugate (as well as all other kit components) at ambient conditions without need for refrigeration and with no need for concern if environmental conditions become hot or humid. Another important effect of the lyophilized product is that it reduces the total number of components needed for application to home diagnostic use utilizing the antibody sandwich enzyme immunoassay technique. Thus a preferred diagnostic kit as described herein need contain only (1) an antibody coated solid support; (2) a vial of lyophilized product containing antibody-enzyme conjugate; (3) a measuring dispenser such as an eye dropper; and (4) vials containing the active components of a chromogenic solution which are admixed prior to use in the assay. Using the measuring dispenser, the user need only dispense a required amount of sample (e.g. urine, suspected of containing the target antigen) into the vial of the lyophilized product containing conjugate. The coated antibody solid support is immediately inserted into the vial containing sample and lyophilized product and gently stirred to form a homogeneous mixture. The mixture is allowed to incubate for a prescribed period at room temperature between about 15° C. to less than 37° C. The antibody coated solid support is removed and washed with cold tap water and then immersed into an activated chromogenic solution. The user need then observe if there is a color change in the chromogenic solution which would indicate the presence of target antigen in the sample. The simplicity of this diagnostic kit stems in part from the additives which applicant has incorporated into the lyophilization product mixture containing conjugate. Applicant has discovered that if a buffered solution containing conjugate in admixture with additives which include a binding enhancing agent to enhance formation of an immune complex, a surfactant and sugar selected from an oligosaccharide, preferably dextrins and trehalose and the solution subsequently lyophilized, the conjugate will maintain reactivity binding specificity and avidity even if subjected to hot and/or humid environmental conditions. The binding enhancing agent, which accelerates formation of an immune complex with the conjugate, is a non-ionic water soluble polymer advantageously selected from polyethylene glycol, polyvinyl alcohol, polyvinyl pyrrolidone and dextran. The preferred binding enhancing agent has been determined to be polyethylene glycol. Buffer components should be selected so that the final solution has a pH of between about 7.2 and 7.6. Preferred buffer components include Hepes salt and Hepes acid and advantageously include a chelating agent such as EDTA disodium and preferably a salt of a polyvalent metal, preferably a salt containing magnesium ion such a crystalline magnesium sulfate.

Other chelating agents (sequestering agents) such as ethylene diamine tetra-acetic acid (EDTA), citric acid, tartaric acid, glucuronic acid, saccharic acid or suitable salts of these acids are enumerated in U.S. Pat. No. 4,228,240 and could possibly be substituted for EDTA disodium. However, in the context of the present invention EDTA disodium is preferred. Also other polyvalent metallic ions as described in U.S. Pat. No. 4,228,240 could possibly also be employed but in the context of the present invention, use of magnesium ion is preferred if a polyvalent metallic salt is employed. Applicants of the present invention have also found it possible to eliminate both the polyvalent metallic ion component and chelating agent from the lyophilization product mixture containing conjugate.

Surprisingly, applicant has found that inclusion of suitable oligosaccharides preferably containing disaccharides (but not sucrose) and more preferably containing dextrin or trehalose sugars have been determined to be important components in the lyophilization mixture. The criticality associated with the selection of specific class of sugars has been surprising. It has been determined that the appropriate class of sugar must exhibit a number of unique properties simultaneously. The appropriate sugar must be rapidly soluble in water preferably dissolving in less than one minute. The sugar must also have the property that it provides a visually homogeneous, stable solid mixture, i.e. a homogeneous stable matrix, of the lyophilized product containing conjugate. Thus the desired class of sugar must produce a uniform, stable, homogeneous solid mixture upon lyophilization. Discovery of suitable sugars having the requisite combination of properties has proved very difficult. Most sugars and also sucrose have been found to be unsatisfactory because they do not produce a homogeneous stable, solid mixture, i.e., stable homogeneous matrix, upon lyophilization, but rather produce concentration gradients of individual components in the lyophilized product. The concentration gradients in turn, have a deleterious effect on the conjugate antibody as the conjugate is exposed to these gradients in the lyophilized product. Suitable sugars are advantageously selected from the class of oligosaccharides and more preferably include disaccharides. Sugars having the requisite property of preventing occurrence of discernible concentration gradients of components in the lyophilized mixture are more readily selected from these classes of sugars. However, it is not fully understood why so distinctly favorable results have been obtained with the use of dextrins and trehalose sugars. These species may have physiochemical properties which impart markedly greater stability and homogeneity to the lyophilized mixture.

The surfactant should be selected from the class of water soluble nonionic surface active agents. The surfactant can be selected from a wide variety of soluble nonionic surface active agents. However, it has been determined that the most suitable surfactants are available under the IGEPAL (octylphenoxypoly (ethylene oxy) ethanol) tradename from GAF Company. Preferred IGEPAL liquid nonionic surfactants are IGEPAL CA 720, IGEPAL CA 630, AND IGEPAL CA 890. Another class of suitable non-ionic surfactant is available under the tradename TETRONIC 909 from BASF Wyandotte Corp. (TETRONIC 909 is a tetrafunctional block copolymer surfactant terminating in primary hydroxyl groups). Another class of suitable nonionic surfactant is available under the VISTA ALFONIC tradename from Vista Chemical Company. VISTA ALFONIC surfactant are ethoxylates which are nonionic biodegradables derived from linear primary alcohol blends of various molecular weights. These nonionic surfactants are most suitable because they provide the appropriate amount of detergency for the assay without having a deleterious effect on the conjugate.

In view of the extreme sensitivity of immunologic components to both environmental condition and chemical environments, the difficulty of achieving a lyophilized product having the properties described herein should be manifest. By inclusion of a surfactant, e.g. a detergent active component into the lyophilized product applicant has eliminated the need to include a detergent as a separate component separated from the immunologic reagents as is typically done in conventional immunoassay kits. Thus with the immunodiagnostic kit of the present invention, the user need wash the solid support with only cold tap water since the detergent active component is already incorporated into the lyophilized product. Applicant, however, was confronted with the difficult problem that surfactants as well as polyethylene glycol by themselves have deleterious effects on the conjugate and, in fact, tend to kill the conjugate reactivity.

Prior art teaches that surfactants, e.g., detergent active agents should be kept separated from the conjugate. Since the conjugate is so sensitive to such components, it has been a difficult problem in exposing conjugate to them without adversely affecting the conjugate's binding properties. Applicants have made the specific discovery that conjugate may be exposed to both a surface active component and polyethylene glycol in the lyophilization solution provided specific sugars, e.g., dextrins or trehalose sugars are included as additives into the lyophilization solution containing conjugate.

In another aspect of the invention, the solid support, typically a dipstick, is coated with a first antibody at ambient conditions of between 15° C. to less than 37° C. to effect adsorption. The coated solid support is then treated with a blocking solution also at room temperature conditions of between 15° C. to less than 37° C. to block remaining adsorption sites and thus prevent non-specific binding of immunologic reagents to the solid support surface. Treatment of the antibody coated solid support with blocking solution has resulted in an additional important advantage. The blocking solution employed by applicant has unexpectedly made the first antibody adsorbed to the solid support resistant to hot, humid environmental condition which may be encountered during transit of the coated support in warm climates or during warehouse storage when temperature and humidity levels may be elevated. Resistance to hot, humid environmental conditions is important if the antibody coated solid support is to be employed as a component in a immunodiagnostic kit, an objective of the present invention. It has been determined that the blocking solution employed in the present invention essentially completely preserves the first antibody's reactivity, binding specificity and avidity for its immunologic binding partners even though the antibody may be exposed to hot environmental conditions, e.g. between about 80° F. to 120° F.

The blocking solution which has resulted in the above described advantages contains a blocking agent and a sugar component in physical admixture. The sugar component is preferably sucrose but can be selected from polysaccharides, oligosaccharides including disaccharides as well as monosaccharides provided the specie selected or any mixture containing different species of the above classes of sugars is water soluble. Examples of suitable monosaccharides are glucose and fructose. Examples of suitable disaccharides are sucrose, maltose, trehalose and lactose and a suitable saccharide mixture is dextrin. It has been determined that the blocking agent to be employed in combination with the above described sugars are advantageously selected from bovine serum albumin (BSA), gelatin, milk protein, or normal nonspecific IgG antibody. Presently the preferred blocking components are bovine serum albumin and milk protein.

DETAILED DESCRIPTION

The various immunoassays of the preferred embodiment are of the ELISA type or "enzyme-linked immunosorbent assay", which is characterized by the separation of the assay materials into solution phase and solid phase components. Various enzyme-linked immunosorbent assay methods are illustrated in A. Voller, et al., "The Enzyme-Linked Immunosorbent Assay", Dynatech Laboratories, Inc., Alexandria, Va. (1979). These assays are advantageously employed for the detection of particular antigens or antibodies which may be present in unknown concentration in a test sample. The preferred, antibody sandwich technique is discussed generally by Voller at pages 13–15. Applicants have found, however, that the protocol described by Voller (at pp. 24–25) of repeated incubations of assay reagents with the solid carrier, with intervening washings of the carrier, raises various difficulties in the implementation of efficient, reliable enzyme immunosorbent assays. The assays disclosed herein overcome these difficulties through essentially simultaneous incubation with the solid phase of the test solution and the enzyme conjugate. In other words, there is no separation of solid and liquid phases between supplying the test solution and the enzyme conjugate.

In this regard, the preferred antibody sandwich assay protocol is effected by admixing a sample suspected of containing the analyte, e.g., antigen being assayed with an antibody-enzyme conjugate and then immediately immersing an antibody coated solid support into the mixture. The coated support is incubated at ambient conditions between 15° C. to less than 37° C. and then washed with tap water to remove unbound material from the support surface. The washed solid support is then immersed in an activated chromogenic solution and a color change in the chromogenic solution is awaited to indicate the presence or absence of analyte in the test sample. In the embodiment at least one and preferably both antibodies are monoclonals against the analyte being assayed.

Although the present preferred methods are applicable to the measurement of a wide variety of specific antigens and antibodies, they have been found of particular utility in home diagnostic kits for detection of antigens such as human chorionic gonadotropin hormone (hCG), present in the urine of pregnant women; Neisseria gonorrhea, the bacteria causing gonorrhea, also called gonococcus (GC); and human leutinizing hormone (hLH), present in female urine at the time of ovulation. The methods of the invention have been extended to include clinical detection of the above antigens.

A principal limiting factor of the sensitivity of enzyme immunoassays disclosed herein is the quality of antisera employed. It is desirable to utilize antibodies of high specificity for the antigen being assayed. In this regard, the use of multispecific substances may decrease assay reliability. A preferred source of monospecific antibody is found in the hybridoma technique, which yields high concentrations of single (monoclonal) antibody molecules having a specific binding site and constant affinity.

In antibody sandwich assays for antigens such as hCG and hLH, the first and second antibodies may be prepared in like manner typically from mouse monoclonal or rabbit polyclonal antisera generated for inoculation of mouse or rabbit with the test antigen. The antibodies are typically purified by gel chromatography and salt precipitation. The second antibody normally binds the antigen molecule at determinants which are different than those at which the first antibody binds to the antigen.

The first and second antibodies may in many cases be used interchangeably in the assay. In the double antibody sandwich ELISA of the preferred embodiment, the first antibody need not be specific for the antigen to be detected; it is necessary only that either the first or second antibody be specific for the antigen. If the antigen to be assayed is Neisseria gonorrhea, the first and second antibodies may be prepared in like manner typically from mouse monoclonal or polyclonal antibody generated from inoculation of a mouse with the GC antigen. In this case, the first and second antibodies need not be directed against different binding sites on the antigen molecule. These first and second antibodies may also be typically used interchangeably in the assay. It should also be appreciated that other binding materials such as lecithin can be used in place of either the first or second antibodies or wherever else antibodies are used in the assay whether to coat the solid support or link the assay antigen to enzyme so long as the substance provides desired binding specificity.

It is an important objective of the present invention to provide an enzyme immunoassay which can be applied in a home diagnostic kit. In keeping with this objective, one important aspect of the invention assures that all immunologic reagents employed in the assay have the property that their reactivity, immunologic binding specificity and avidity are essentially completely preserved even though these immunologic reagents to be included as kit components may be exposed to hot, humid environmental conditions during transit, or prior to use in the assay. In particular, one aspect of the invention provides as one of the kit components a lyophilized product mixture which contains therein an antibody-enzyme conjugate one of the active immunologic reagents to be utilized in the assay. The lyophilized product mixture contains therein additives which are first blended in lyophilization solution together in admixture with the conjugate. The lyophilization solution containing conjugate and additives is subjected to freeze drying forming a powdered lyophilized freeze dried product. The effect of the lyophilized product mixture of the invention containing antibody-enzyme conjugate is multifold. The additives included in admixture with the conjugate in the lyophilized product have been determined to preserve the reactivity, binding specificity and avidity of the conjugate when applied to the assay even if the lyophilized product containing conjugate is subjected to hot environmental conditions between 80° F. to 120° F. In practical terms, this means that the conjugate can be included in the diagnostic kit without concern that its reactivity or immunologic binding specificity will be lost if the kit components are exposed to hot, humid environmental conditions. Additionally, the user may feel free to store the lyophilized product containing conjugate (as well as all other kit components) at ambient conditions without need for refrigeration and with no need for concern if environmental conditions become hot or humid. Another important effect of the lyophilized product containing conjugate is that it reduces the total number of components needed for application to home diagnostic use utilizing the antibody sandwich enzyme immunoassay technique. Thus a preferred diagnostic kit as described herein need contain only (1) an antibody coated solid support; (2) a vial of lyophilized product containing antibody-enzyme conjugate; (3) an eye dropper; and (4) vials containing the active components of a chromogenic solution which are admixed prior to use in the assay. Using the eyedropper the user need only dispense a required amount of sample (e.g. urine, suspected of containing the target antigen) into the vial of the lyophilized product containing conjugate. The coated antibody solid support is immediately inserted into the vial containing sample and lyophilized product and gently stirred to form a homogeneous mixture. The mixture is allowed to incubate for a prescribed period at room temperature between about 15° C. to less than 37° C. The antibody coated solid support is removed and washed with cold tap water and then immersed into an activated chromogenic solution. The user need then observe if there is a color change in the chromogenic solution which would indicate the presence of target antigen in the sample. The simplicity of this diagnostic kit stems in part from the additives which applicant has incorporated into the lyophilization product mixture containing conjugate. Applicant has discovered that if a buffered solution containing conjugate in admixture with additives which include a binding enhancing agent to enhance formation of an immune complex, a surfactant and sugar preferably selected from dextrins and trehalose and the solution subsequently lyophilized the conjugate will maintain reactivity binding specificity and avidity even if subjected to hot and/or humid environmental conditions prior to its use in the assay. Applicant has determined that the agent which enhances the binding characteristics of the conjugate, i.e., enhances the formation of an immune complex with the conjugate, is a nonionic water soluble polymer advantageously selected from polyethylene glycol, polyvinyl alcohol, polyvinyl pyrrolidone, and dextran. The preferred binding enhancing agent has been determined to be polyethylene glycol. Specifically in an antibody sandwich assay, these binding enhancing agents, particularly polyethylene glycol, facilitate and enhance binding of the antibody-enzyme conjugate to the antigen being assayed and also facilitate and enhance binding of the antigen to the antibody coated on the solid support. Buffer components should be selected so that the final solution has a pH of between about 7.2 and 7.6. Preferred buffer components include Hepes salt and Hepes acid and advantageously include a chelating agent such as EDTA disodium and preferably a salt of a polyvalent metal, preferably a salt containing magnesium ion such as crystalline magnesium sulfate.

Other chelating agents (sequestering agents) such as ethylene diamine tetra-acetic acid (EDTA), citric acid, tartaric acid, glucuronic acid, saccharic acid or suitable salts of these acids are enumerated in U.S. Pat. No. 4,228,240 and could possibly be substituted for EDTA disodium. However, in the context of the present invention EDTA disodium is preferred. Also other polyvalent metallic ion as described in U.S. Pat. No. 4,228,240 could possibly also be employed but in the context of the present invention use of magnesium ion is preferred if a polyvalent metallic salt is employed. However, in the context of the present invention, it has been found possible to eliminate both the polyvalent metallic ion and chelating agent from the lyophilization solution and yet attain about the same effect in preservation of conjugate reactivity and binding specificity. (See Example 5).

Surprisingly applicant has found that inclusion of suitable oligosaccharides preferably containing disaccharides (but not sucrose) and, more preferably containing dextrin or trehalose sugars are important components in the lyophilization mixture. The criticality associated with the selection of specific classes of sugars has been surprising. It has been determined that the appropriate class of sugar must exhibit a number of unique properties simultaneously. The appropriate sugar must be rapidly soluble in water preferably dissolving in less than one minute. The sugar must also have the property that it provides a visually homogeneous, stable solid mixture, i.e. a homogeneous stable matrix, of the lyophilized product containing conjugate. Thus the desired class of sugar must produce a uniform, stable, homogeneous solid mixture upon lyophilization. Discovery of suitable sugars having the requisite combination of properties has proved very difficult. Most sugars and also sucrose have been found to be unsatisfactory because they do not produce a homogeneous stable, solid mixture, i.e., stable homogeneous matrix, upon lyophilization, but rather produce concentration gradients of individual components in the lyophilized product. The concentration gradients in turn, have a deleterious effect on the conjugate antibody as the conjugate is exposed to these gradients in the lyophilized product. Suitable sugars are advantageously selected from the class of oligosaccharides and more preferably include disaccharides but not sucrose. Sugars having the requisite property of preventing occurrence of discernible concentration gradients of components in the lyophilized mixture are more readily selected from these classes of sugars. However, it is not fully understood why so distinctly favorable results have been obtained with the use of dextrins and trehalose sugars. Dextrin is a mixture of glucose, the disaccharide maltose, and higher molecular weight saccharides. Trehalose is a disaccharide containing two D-glucose residues. Dextrin and trehalose appear to have physiochemical properties which impart markedly greater stability and homogeneity to the lyophilized mixture.

The surfactant should be selected from the class of water soluble nonionic surface active agents. The surfactant can be selected from a wide variety of soluble nonionic surface active agents. However, it has been determined that the most suitable surfactants are available under the IGEPAL (octylphenoxypoly (ethylene oxy) ethanol) tradename from GAF Company. Preferred IGEPAL liquid nonionic surfactants are IGEPAL CA 720, IGEPAL CA 630, AND IGEPAL 890. Another class of suitable nonionic surfactants is available under the tradename TETRONIC. 909 from BASF. Wyandotte Corp. (TETRONIC. 909 is a tetrafunctional block copolymer surfactant terminating in primary hydroxyl groups). Another class of suitable nonionic surfactant is available under the VISTA ALFONIC tradename from Vista Chemical Company. VISTA ALFONIC surfactant are ethoxylates which are nonionic biodegradables derived from linear primary alcohol blends of various molecular weights. They are essentially 100 per cent active and have the following general structural formula: $CH_3(CH_2)_yCH_2(OCH_2CH_2)_nOH$ wherein y varies between 4 and 16 and n varies between 1 and 11. The above listed nonionic surfactants are most suitable because they provide the appropriate amount of detergency for the assay without having a deleterious effect on the conjugate.

In view of the extreme sensitivity of immunologic components to both environmental conditions and chemical environments, the difficulty of achieving a lyophilized product having the properties described herein should be manifest. The inclusion of a surfactant, i.e., a detergent action component into the lyophilized product applicant has eliminated the need to include a detergent as a separate component in the assay as is typically done in immunoassay kits. Thus with the immunodiagnostic kit of the present invention, the user need wash the solid support with only cold tap water since the detergent active component is already incorporated into the lyophilized product. Applicant, however, was confronted with the difficult problem that detergent active agents as well as binding enhancing agents such as polyethylene glycol by themselves have deleterious effects on the conjugate and in fact tend to kill the conjugate reactivity.

Prior art teaches that detergent active agents in particular should be kept separated from the conjugate. Since the conjugate is so sensitive to these components, it has been a difficult problem in exposing conjugate to these components without adversely affecting the conjugate's binding properties. Applicants have made the specific discovery that conjugate may be exposed to both a detergent active component and the aforementioned binding enhancing agents, particularly polyethylene glycol, in the lyophilization solution provided specific sugars, e.g., dextrins or trehalose sugars are included as additives into the lyophilization solution containing conjugate. The lyophilized product mixture of the present invention containing the conjugate is an important factor in assuring that the binding properties of the conjugate antibody are sufficiently preserved to permit conduct of the assay as described in Example 2 wherein all steps of the assay are conducted under ambient room temperature conditions of between about 15° C. to less than 37° C, thus making the assay suitable for home diagnostic application.

A variety of structures and materials may be employed for the solid carrier. In the ELISA technique the "solid phase" is established by insolubilizing the assay reagents through bonding to the solid carrier. Suitable carrier materials include cellulose, cross-linked dextrose, silicon rubber, microcrystalline glass, and a wide variety of plastics. Particularly suitable structures are preformed such as tubes, disks, and microplates, which have the advantage of being easily washed. The immunologically reactive components may be covalently bonded to the solid support, cross-linked, or physically coupled thereto.

In the preferred embodiment of the invention, the solid carrier comprises a nonporous injection molded polymer article. Polystyrene, polypropylene, polyvinyl chloride, polyamides, and other polymers have been widely employed in such applications, or styrene-acrylonitrile copolymer, commonly known as SAN, as set forth in commonly assigned U.S. application Ser. No. 462,300, filed Jan. 31, 1983 now abandoned.

In coating the solid support, a procedure is adopted in accordance with the coating characteristics of the immunologically active material. Most substances will effectively coat by application in solution and incubation for a reasonably brief period. Certain materials, however, such as bacterial suspensions will not passively adsorb to the solid support, and require a more time-consuming coating procedure whereby the material is allowed to dry on the support surface.

In a preferred embodiment of the invention, the solid support, typically a dipstick is coated with a first antibody at ambient conditions of between 15° C. to less than 37° C. to effect adsorption. The coated solid support is then treated with a blocking solution also at room temperature conditions of between 15° C. to less than 37° C. to block remaining adsorption sites and thus prevent nonspecific binding of immunologic reagents to the solid support surface. Treatment of the antibody coated solid support with blocking solution has resulted in an additional important advantage. The blocking solution employed by applicant has unexpectedly made the first antibody adsorbed to the solid support resistant to hot, humid environmental condition which may be encountered during transit of the coated support in warm climates or during warehouse storage when temperature and humidity levels may be elevated. Resistance to hot, humid environmental conditions is important if the antibody coated solid support is to be employed as a component in a immunodiagnostic kit, an objective of the present invention. It has been determined that the blocking solution employed in the present invention essentially preserves the first antibody's reactivity, binding specificity and avidity for its immunologic binding partners even if the antibody may be exposed to hot environmental conditions, e.g., between about 80° F. to 120° F. prior to its use in the assay. Even at prior exposure to high temperatures, e.g., between 100° F. to 120° F. for a month's duration, it has been determined that the first antibody's reactivity is sufficiently preserved to permit satisfactory conduct of the assay employing the normal assay protocol of the invention, e.g., as described in Example 2. The blocking solution also helps assure that the first antibody's binding properties and reactivity is sufficiently preserved to permit conduct of the assay as described in Example 2 wherein all steps of the assay are conducted under ambient room temperature conditions of between 15° C. to less than 37° C, thus making the assay suitable for home diagnostic application.

The blocking solution which has resulted in the aforementioned advantages contains a blocking agent and a sugar component in physical admixture. The sugar component is preferably sucrose but can be selected from polysaccharides, oligosaccharides including disaccharides as well as monosaccharides provided the specie selected or any mixture containing different species of the above classes of sugars is water soluble. Examples of suitable monosaccharides are glucose and fructose. Examples of suitable disaccharides are sucrose, maltose, trehalose and lactose and a suitable saccharide mixture is dextrin. It has been determined that the blocking agent to be employed in combination with the above described sugars are advantageously selected from bovine serum albumin (BSA), gelatin, milk protein, or normal nonspecific IgG antibody. Presently the preferred blocking components are bovine serum albumin and milk protein.

The choice of a suitable enzyme preparation for the immunosorbent assays of the invention should take a number of factors into account. The enzyme should be of high purity, and its activity should not be inhibited by the other components of the assay, conjugation procedures, and test conditions employed. The enzyme should bind firmly to the molecules to be assayed, or to an intermediary such as biotin. The enzyme should be a stable material, which exhibits a high specificity and turnover rate for the enzyme chromogenic substrate. Additionally, the sample medium (i.e., blood, serum, urine, etc.) should not normally contain the enzyme or its inhibitors. Suitable enzymes include, for example, acetal cholinesterase, alkaline phosphatase, cytochrome C, B-D-glucoronidase, glucoamylase, B-D-galactosidase, glucose oxidase, lactate dehydrogenase, lactoperoxidase, ribonuclease, tyrosinase, and urease.

In the preferred embodiment of the invention, horseradish peroxidase is selected as the tagging enzyme. HRPO possesses excellent characteristics for such purposes as well known in the art, in that it is inexpensive, readily conjugated to a variety of proteins, and includes a wide variety of substrates.

The enzyme is covalently bonded to second antibodies or other bindable proteins so as to preserve a substantial degree of reactivity of each component. One technique commonly employed for this purpose uses a bifunctional cross-linking agent to chemically bridge the enzyme and protein. In a one-step procedure the enzyme, antibody, and cross-linking agent are admixed and interact to generate the conjugate. In a two-step procedure, the enzyme is preliminarily reacted with a cross-linking agent, and then reacted with the bindable substance. For peroxidase conjugation such as with horseradish peroxidase, a variety of bifunctional agents have been employed in such two-step methods including for example p, p' -difluoro-m, m-dinitrodiphenyl sulphone, [1-cyclohexyl-3-(2-morpholinoethyl)] carbodiimide metho-p-toluenesulphonate, cyanuric chloride, bis-diazotized o-dianisidine, and glutaraldehyde. These techniques have generally engendered a relatively low yield of HRPO-IgG polymers due to the scarcity of reactive amino groups in commercially available HRPO.

The preferred conjugation method is that disclosed by Wilson and Nakane, "Recent Developments in the Periodate Method of Conjugating Horseradish Peroxidase (HRPO) to Antibodies", at p. 215 et. seq. of Immunofluorescence and Related Staining Techniques, edited by W. Knapp et al., 1978, Elsevier/North-Holland Biomedical Press. This technique uses sodium periodate to form aldehyde groups in the peroxidase, which in turn react with the amino groups of the antibody to be labelled. As disclosed in the above article, the periodate oxidation may be carried out at low pH to reduce undesirable self-coupling of the HRPO molecules. This conjugation method, by creating a plurality of reactive groups in the HRPO molecule, results in a cross-linked aggregation of these components of high molecular weight (upward of 400,000 M.W.). HRPO-IgG conjugates containing between one and two peroxidase molecules per antibody molecule have been observed to provide high sensitivity with relatively low nonspecific background readings. This conjugation technique has been successfully extended by applicants to the conjugation of IgM and IgA monoclonal antibodies.

All of the above coupling methods result in a final reaction mixture which includes in addition to the HRPO-antibody conjugates, moieties of uncoupled antibody (monomeric and polymeric) and uncoupled enzyme. For best results, regardless of the particular enzyme and immunologic reagent employed, it is desirable to separate the monomeric conjugate from the other reaction products. Residual antibody competes with the labelled antibody in the incubation with antigen and thus lowers assay sensitivity. More seriously, uncoupled enzyme, particularly HRPO, shows a high tendency toward nonspecific adsorption to the solid phase. It is therefore important to purify the conjugates particularly with a view to separating free enzyme. Separation methods which have been successfully employed for this purpose include molecular sieving as by gel chromatography; affinity chromatography; and salt precipitation.

The solution to be tested for presence of a particular analyte may be a urine or serum sample, exudate, or other suitable sample, or may be an aqueous solution of a solid antigen sample such as a cell culture extracted from a solid nutrient medium. The test sample may be dissolved in or supplemented by a buffer to provide a suitable medium for the simultaneous incubations of the invention. In testing for human chorionic gonadotropin (hCG) and leutinizing hormone (hLH) applicants have observed that an additive including polyethylene glycol (PEG) facilitates immunologic reactions of antigen, first antibody, and enzyme conjugate. In certain cases for best results it may be necessary to premix the sample and PEG buffer prior to adding the conjugate. However, as described in the foregoing and in examples 2–5, applicants have found it possible to include PEG into the lyophilization solution along with other additives including a detergent active (surfactant) component. This has eliminated the need to include additives such as PEG and detergent active components in a separate vial when the assay is supplied in a kit form for home diagnostic use. Also the lyophilized mixture containing conjugate as set forth in examples 2–5 preserves the reactivity and binding specificity of the conjugate even if exposed to elevated environmental temperatures between 80° F. to 120° F.

The preferred method for detection of enzyme in the solid phase uses a chromogenic substrate to provide a visible reaction product. The choice of substrate naturally depends on the tagging enzyme. For alkaline phosphatase a convenient substrate is p-nitrophenyl phosphate. A wide variety of peroxidase substrates oxidized by $H_2O_2$ are available; it is desirable to choose one with adequate solubility. Workers in the art have commonly used o-phenylenediamine (OPD).

Applicants have found a particularly suitable chromogen for peroxidase assays in tetramethylbenzidine (TMB) and its water soluble chemical derivatives as disclosed in detail in commonly assigned U.S. Pat. No. 4,503,143.

In home and clinical diagnostic applications using colorimetric detection of enzyme, the user may register the presence of a specific antibody or antigen qualitatively simply by observing the presence of color in an immunoassay sample containing even trace amounts of the subject antibody or antigen. This subjective observation may be assessed quantitatively as "Positive" when the absorbance or optical density at the maximum absorbance wavelength (in the range 620–700 nm for TMB) exceeds a predetermined threshold level nominally on the order of two standard deviations above a negative threshold, illustratively about 0.04. Thus, the method of the invention may be employed in clinical analysis to obtain quantitative measurement of a specific antibody or antigen in the test sample. Quantitative measurement is obtained spectrophotometrically by reading the absorbance at maximum absorbance wavelength.

Although the enzyme immunosorbent assay technique of the preferred embodiment utilizes a colorimetric detection technique to measure the tagging enzyme, it is possible to use a variety of optical detection techniques in the ELISA's of the invention. Alternative techniques include, for example, ultraviolet radiation detection, and fluorescent tagging of the enzyme.

The invention is further illustrated in the following nonlimiting examples of enzyme immunosorbent assays according to the above-described methodology. All parts are by weight unless otherwise specified.

EXAMPLE 1

The following protocol was carried out as a colorimetric antibody sandwich ELISA for human chorionic gonadotropin hormone (hCG). The procedure involved coating a solid support with a first antibody, adding an antigen sample and simultaneously supplying a second-antibody enzyme conjugate, separating the solid and solution phases, and finally furnishing a color indicator for the solid phase. The first and second antibodies were monoclonal antibodies obtained from inoculated mice. The first (coating) antibody was a nonspecific monoclonal antibody raised against hCG, of the IgG class, while the second antibody was a beta chain-specific anti-hCG hybridoma, of the IgM class. First and second antibodies were purified using an Ultrogel AcA 34 column chromatography (Ultrogel AcA 34 is a trademark of LKB Instruments Inc., Rockville, Md.).

A styrene-acrylonitrile (SAN) copolymer dipstick was coated with the first antibody by incubation for one hour at 23° C.±2° C. in a beaker with 12.5 micrograms per milliliter of the antibody in phosphate buffered saline (PBS); available in calcium-free form from GIBCO Laboratories, Grand Island, N.Y. The antibody solution was then decanted, and the dipstick incubated for thirty minutes at 23° C. with a blocking solution of 3.0 ml PBS/0.5% BSA/20% sugar (0.5 gms BSA and 20 gm sugar per 100 ml of PBS). The PBS component is phosphate buffered saline and the BSA component is BSA (bovine serum albumin) Cohn Fraction V, supplied by Sigma Chemical Co., St. Louis, Mo.

The sugar employed in the blocking solution is preferably sucrose but can be selected from polysaccharides, oligosaccharides including disaccharides as well as monosaccharides provided the specie selected or mixture of different sugars is water soluble. Typical examples of suitable monosaccharides are glucose and fructose. Typical disaccharides are sucrose, maltose, trehalose and lactose; and typical suitable saccharide mixture is dextrin. Instead of bovine serum albumin (BSA) the blocking solution may contain gelatin, milk protein, or normal nonspecific IgG antibody. Presently bovine serum albumin (BSA) and milk protein are preferred.

The second antibody was covalently conjugated to the enzyme horseradish peroxidase (HRPO) according to the periodate method, as follows:

Four milligrams horseradish peroxidase (type VI obtained from Sigma Chemical Co., St. Louis, Mo.) was dissolved in 1 mL. deionized water. One milliliter freshly prepared 0.1 M NaIO4 was added and stirred for twenty minutes at room temperature. The resulting solution was adjusted to pH 4.4 in a 1 mM sodium acetate buffer by dialysis. The pH was then readjusted to 9.5 by adding 20 microliters. 0.2 M carbonate buffer (pH 9.5), and 8 mg of the anti-hCG second antibody in 0.01 M carbonate buffer, pH 9.5, was added immediately. The reaction mixture was stirred for 2 hrs. at room temperature and 0.1 ml of freshly prepared sodium borohydride solution in a dilution of 4 mg/ml water added. The mixture was then left for two hours at 4° C.

The resulting reaction mixture was then purified by adding an equal amount of saturated ammonium sulfate (SAS) solution, washing once with 50 percent SAS, and dialyzing against phosphate buffered saline. Aliquots of the purified conjugate were lyophilized without including additional additives to the purified conjugate. The lyophilized conjugate was stored in a glass lyophilization vial.

An antigen test solution was formulated by diluting a urine sample to be tested for hCG in a buffer containing polyethylene glycol (PEG) and polyoxyethylenesorbitan monolaurate (a detergent available under the tradename Tween 20 from Sigma Chemical Co., St. Louis, MO), resulting in a final concentration of 0.25% Tween 20, 2% PEG. One milliliter of the test solution was added to the lyophilization vial, which was agitated to reconstitute the conjugate in the test solution.

The coated dipstick was inserted in the lyophilization vial and incubated for thirty minutes at room temperature. The stick was then removed and washed for thirty seconds in cold tap water. The dipstick was then placed in 400 ml of a tetramethylbenzidine color indicator solution prepared as disclosed in commonly assigned U.S. Pat. No. 4,503,143 by mixing 4.0 parts by volume of reagent (i) with 11.0 parts by volume of reagent (ii), and then adding 0.010 part by volume of the 30 percent hydrogen peroxide solution (reagent (iii)). The mixture was stirred to form a homogeneous, activated TMB solution.

Reagent (i) was prepared by dissolving 1.25 g (5.20 mM) of 3,3',5,5'-tetramethylbenzidine in 1.00 liter absolute methanol with or without heating. A clear colorless or faintly tan solution resulted which could be stored for at least six weeks in a brown bottle without affecting its usefulness.

Reagent (ii) was a buffer prepared by first dissolving 144.8 grams (1.020 M) of disodium hydrogen phosphate in 1.00 liter hot deionized water. The phosphate dissolved in the hot deionized water upon stirring. To this solution 102.95 grams (0.4902 M) of citric acid monohydrate were added. The resulting solution was then diluted to 10.0 liters with additional deionized water, thus forming a citrate-phosphate solution, with a pH of 5.0.

Reagent (iii) consisted of an aqueous solution of hydrogen peroxide, wherein the $H_2O_2$ comprised 30 percent by volume.

The dipstick and chromogen solution were incubated for ten minutes at 23° C. The presence of blue color in the dipstick would provide a qualitative indication of the presence of hCG in the sample; a positive reading was indicated by a strong blue color. A quantitative measurement was made by placing 300 microliters of the chromogen solution in a microtiter plate after removing the dipstick to stop the reaction, and reading the absorbance at 660 nanometers with a Dynatech Microelisa MR580 Autoreader, available from Dynatech Laboratories, Alexandria, Va. This protocol was successfully employed by unskilled users to visually detect hCG hormone at concentrations of 50 mIU/mL. Clinical tests with several hundred subjects gave 100 percent success in the reference negative samples, and 98 percent success in the positive samples.

Although the assay protocol described in this example can be reduced to home diagnostic application in kit form, the resulting kit would need to have included therein a separate vial for the buffer solution containing polyethylene glycol (PEG) and detergent, e.g. polyoxyethylene sorbitan monolaurate (Tween 20). The user would be required to add this solution to the test sample in a separate step before the test sample was added to the lyophilization vial containing lyophilized conjugate as described in the above protocol (Example 1). Additionally there is risk that the conjugate if lyophilized in pure form could lose reactivity or binding specificity if exposed to hot, humid environmental conditions during prolonged storage.

EXAMPLE 2

The following examples 2–4 describe the preferred assay protocol of the invention wherein additives such as polyethylene glycol and a surfactant, e.g. a detergent active component have been incorporated into the lyophilization product mixture containing the conjugate. Thus, the assay protocols set forth in examples 2–4 can be reduced to home diagnostic application in kit form as in Example 6 thus eliminating the need for supplying a separate vial containing polyethylene glycol (binding enhancing agent) and detergent active component, e.g. Tween 20 as referenced in the protocol set forth in Example 1. The following assays have the additional advantage over that described in Example 1 in that the conjugate is better protected against loss of reactivity and loss of binding specificity if exposed to hot, humid environmental conditions during storage.

Separate assays for HCG and LH hormone were conducted employing the sandwich enzyme method described in the foregoing. The first and second antibodies in both the HCG and LH assays were derived from hybridoma cells producing monoclonal antibodies in vivo within ascites fluid or in vitro contained in supernatent fluid of tissue cultured cells. These hybridoma cells were in turn produced from the fusion of spleen cells and myeloma cells. The spleen cells (lymphocyte cells) were obtained from mice inoculated with commercially available preparation of the above mentioned HCG or LH hormones. Specific monoclonal antisera for the assays are produced from hybridoma cultured in vivo in ascites fluid or in vitro in the supernatent fluid. In the HCG and LH assays both the first and second antibodies were monoclonal antibodies. In both the HCG and LH assays the second antibody, i.e. the antibody bound to enzyme (peroxidase) to form the conjugate was selected to be the same.

The second antibody was conjugated to peroxidase enzyme in each case to form the antibody enzyme conjugate. The conjugate was produced employing the periodate technique for example as described in Example 1. Leutinizing hormone (LH) served as the antigenic stimulus for mice for the production of the first monoclonal antibody used in the LH assay.

Conversely HCG hormone served as the antigenic stimulus for mice for the production of the first monoclonal antibody used in the HCG.

The dipsticks were coated with first antibody: a coating solution was prepared (consisting of glycine at pH 3.0), and this was added to a vessel which contained the dipsticks properly aligned. After four hours, incubation at room temperature between 15° C. to less than 37° C. the solution was drained.

Remaining adsorption sites were blocked by thirty minutes to one hour room temperature incubation with a blocking solution of 3.0mL PBS/0.5% BSA/20% sugar, e.g. sucrose (0.5 gm BSA and 20 gm sugar per 100 ml PBS). The sugar employed in the blocking solution is preferably sucrose but can be polysaccharides, oligosaccharides including disaccharides as well as monosaccharides provided the specie selected or mixture of different sugar is water soluble. Typical examples of suitable monosaccharides are glucose and fructose. Typical disaccharides are sucrose, maltose, trehalose and lactose; and typical suitable polysaccharides are dextrins. Instead of bovine serum albumin (BSA) the blocking solution may contain gelatin, milk protein, or normal non-specific IgG antibody. Presently bovine serum albumin (BSA) and milk protein are preferred. The use of the blocking solution as above described has been found to stabilize the first antibody so that the antibody does not lose its reactivity or binding specificity if the coated dipstick is exposed to hot, humid environmental conditions during transit or storage. The blocking solution was allowed to react for 1 hour. Depending upon the size of the vessel, the volume of blocking solution to use is mandated by the area on the dipstick to be coated and blocked. The area that is coated with antibody is the active region and also the absolute minimum area that must be involved in the blocking stage.

Excess solution which "wets" the dipstick is removed by a gentle centrifugation step. A drying step is then employed to evaporate and thus remove any liquid remaining on the coated and blocked dipsticks.

The product that emerges is not in liquid form but in a solid mass resembling the interior of the contaminant vessel.

The biological sample to be tested for antigen, e.g., a urine sample in an assay for HCG or LH hormone was added in a measured quantity of 0.8 ml directly to the lyophilized product containing conjugate. (See examples 3 and 4 for the preparation of lyophilized product mixture containing conjugate). The lyophilized product was immediately reconstituted and dissolved to form a homogeneous mixture when the biological sample and lyophilized product containing conjugate were admixed. Therefore, immediately upon admixture of the sample and lyophilized product the antibody coated dipstick was inserted and the total mixture gently stirred.

The coated dipstick was left immersed in the homogeneous solution containing the sample and reconstituted lyophilized product containing the conjugate. The immersion period, i.e., the incubation period, is at least 15 minutes and is carried out at ambient room temperature condition between about 15° C. to less than 37° C. Upon completion of the incubation period a solid phase matrix antibody—antigen—conjugate sandwich is formed on the dipstick.

The dipstick is then removed from the homogeneous solution and washed using cold tap water to remove any material not specifically bound to the solid matrix.

An activated chromogenic solution is prepared in accordance with the protocol set forth in Example 1. The washed dipstick is then added to the solution which will change from colorless to blue-green. The degree of color intensity (darkness) reflects the concentration of bound antigen in our sample. The color change reaction is allowed to occur over a 5 minute period and is then halted by the removal of the dipstick. The color intensity is determined in an objective manner by use of a spectrophotometer or can be subjectively determined by comparison to a standardized color chart.

EXAMPLE 3

The lyophilized product containing conjugate which product was used in the assays referenced in Example 2 was prepared as follows:

A preferred lyophilization solution to which the conjugate was to be added was first prepared as follows:

40 gm of polyethylene glycol (PEG 8000 from Fischer Chemical); 16.6 gm of Hepes Salt (Research Organics); 19.2 gm of Hepes Acid (Research Organics); 1.4 gm EDTA disodium (Sigma Chemical); 1 gm of magnesium sulfate crystalline (Sigma Chemical Company) and 200 gm dextrins (Maltrin brand sugar from Grain Processing Corp.) are added to 1 liter of distilled water. The solution is mixed until all of the above components (particulates) are dissolved and then to that mixture is added 6 mL of liquid surfactant available under the trade name IGEPAL CA-630 from Sigma Chemical. IGEPAL CA-630 surfactant is composed of octylphenoxypoly (ethylene oxy) enthanol).

Upon complete dissolution, the final homogeneous solution is brought up to 2 liters volume by adding a sufficient volume of distilled water. The resulting solution had a final pH in the range of 7.2 to 7.5. The lyophilization solution was then aseptically filtered through a 0.45 micron filter and may be stored under sterile conditions at 4° C.

A titered antibody-enzyme conjugate as described in Example 2 was then added to the filtered lyophilization solution resulting in a final lyophilization solution containing conjugate. For end use in the LH assay sufficient conjugate was added to the above filtered lyophilization solution so that the concentration of conjugate therein is in a range between about 0.10 to 0.25 micro gm/mL.

For end use in the HCG assay sufficient conjugate was added to the above described filtered lyophilization solution so that the conjugate therein has a concentration in a range between about 0.2 to 0.4 micro gm/mL.

The final lyophilization solution containing conjugate was then subjected to lyophilization to form the lyophilized product mixture to be used in the assay. Approximately 0.8 mL of the lyophilization solution containing conjugate was first dispensed to the vials which are then loosely capped in preparation of the lyophilization procedure. (The glass vials are of a diameter just large enough to permit insertion of the coated dipstick during conduct of the assay.)

The lyophilization cycle that has been found to be preferable first requires the freezing of the lyophilization solution containing conjugate. The solution was freezed in a conventional lyophilization chamber maintained at a temperature range between about $-40°$ C. and $-35°$ C. for at least two hours at atmospheric conditions. The frozen lyophilized solution containing conjugate was then subjected to vacuum pressure of about 10 to 50 mili torr over a 24 hour period. During this 24 hour cycle the temperature in the lyophilization chamber is adjusted to incremental levels while the high vacuum conditions were maintained at about 10 to 50 mili torr. Typical temperature levels employed during the lyophilization cycle were $-10°$ C. for 18 hrs.; and $+25°$ C. for about 7 to 10 hours until the product reaches about 25° C. The lyophilization chamber was then partially filled with nitrogen and the vials containing the lyophilized product were stoppered. During the lyophilization cycle all liquid in the lyophilization solution evaporates. The resulting lyophilized product containing conjugate is a freeze dried product in powdered form ready for use in the assays described in Example 2.

EXAMPLE 4

Alternatively, another preferred lyophilized product was prepared in the identical manner as set forth in Example 3 except that the lyophilization solution was prepared in the following manner:

40 gm of polyethylene glycol (PEG 8000 from Fisher Chemical Company); 16.6 gm Hepes Salt (Research Organics); 19.2 gm Hepes Acid; 1.4 gm EDTA disodium; 1.0 gm magnesium sulfate crystalline and 240 gm trehalose sugar (Sigma Chemical) were added to 1 liter of distilled water. After all the components (particulate) were completely dissolved upon mixing, 5 ml of IGEPAL CA 720 liquid surfactant from Sigma Chemical was added while mixing. [IGEPAL CA 720 surfactant is composed of octylphenoxypoly (ethylene oxy) ethanol]. The final volume of the solution was brought up to two liters by adding distilled water. The resulting solution had a pH in the range between about 7.2 to 7.5. The lyophilized solution was then aseptically filtered through a 0.45 micron filter. Conjugate as described in Example 2 was then added to the filtered lyophilization solution. As in Example 3, sufficient conjugate was added to that the concentration of conjugate in the solution was between about 0.10 to 0.25 micro-gm per mL of the enzyme in the conjugate for end use in the LH assay and between about 0.2 and 0.4 micro gm per mL of enzyme for end use in the HCG assay.

The lyophilized solution containing conjugate was then frozen in a lyophilization chamber at a temperature between about $-40°$ C. to $-35°$ C. for at least 2 hours and subjected to the lyophilization cycle as described in Example 3. The resulting lyophilization product mixture containing conjugate was then ready for use in the assays described in Example 2.

EXAMPLE 5

Alternatively, another preferred lyophilization solution and lyophilization product for use in the assay protocol of Example 2 were prepared in the identical manner as set forth in Example 3 except that polyvalent ion (magnesium sulfate) and chelating agent (EDTA disodium) were both not included in the lyophilization solution. All other components and quantities for preparation of the lyophilization solution and lyophilized product were identical to that set forth in Example 3. The reactivity and binding specificity of the conjugate antibody in this Example 5 was determined to be preserved about as well as in Example 3, even though polyvalent ion (magnesium sulfate) and chelating agent were both absent from the lyophilization solution.

EXAMPLE 6

In a preferred assay kit specifically for home diagnostic use, the kit has the following components:

(1) a vial #1 of lyophilized product mixture containing conjugate which product was prepared in accordance with Example 3, 4 or 5;

(2) a dipstick coated with first antibody and subsequently treated with blocking solution, e.g., as described in example 2;

(3) a measuring dispenser, e.g., an eye dropper;

(4) a squeeze tube containing buffer and peroxide;

(5) a vial #2 containing chromogen and solvent.

The user conducts the assay for antigen, e.g., for HCG or LH hormone under room temperature conditions using the kit components. Using the eye dropper the user first measures out a specified amount of urine sample suspected of containing the antigen being assayed. The user dispenses the measured sample into the vial #1 containing the lyophilized product mixture. The conjugate is immediately reconstituted. The antibody coated dipstick is then immediately immersed into the vial #1 containing the sample and reconstituted conjugate. The dipstick is gently stirred until a homogeneous solution is achieved. The antibody coated dipstick is allowed to incubate for 15 minutes in this solution at room temperature between 15° C. to less than 37° C. The dipstick is then removed and washed with cold tap water. The user prepares an activated chromogenic solution by squeezing the contents of the squeeze tube, i.e. the buffer and peroxide into the vial #2 which contains chromogen and solvent. The dipstick which has been washed with cold tap water is immersed into vial #2 now containing the activated chromogenic solution for 5 minutes and the user observes if a color change has occurred, thus determining the presence of antigen being assayed.

Although the enzyme immunoassay techniques of the invention have been illustrated in the foregoing detailed description in the context of certain specific enzyme linked immunosorbent assays, it should be appreciated that they may be extended to a variety of enzyme immunoassays. Accordingly, the invention is not intended to be limited to the specific embodiments or examples set forth in the specification, but rather is defined by the claims and equivalents thereof.

What is claimed is:

1. In a lyophilized mixture for use in an enzyme immunoassay, said mixture comprising an antibody-enzyme conjugate and buffer salts, wherein the improvement comprises that said enzyme in said antibody-enzyme conjugate comprises peroxidase and that said lyophilized mixture further comprises:
   (a) a binding enhancing agent selected from the group consisting of polyethylene glycol, polyvinyl alcohol, polyvinyl pyrrolidone and dextran;
   (b) a water soluble non ionic surfactant, said surfactant being present in the mixture in an amount sufficient to provide an appropriate amount of detergency for said immunoassay without having a deleterious effect on the conjugate; and
   (c) a sugar selected from the group consisting of dextrin and trehalose, said sugar being present in the mixture in an amount sufficient to prevent discernible concentration gradients of the components in said mixture;
said lyophilized mixture having the property of preserving the antibody reactivity and the immunologic binding specificity of the antibody-enzyme conjugate even if the mixture is exposed to temperatures between about 80° F. and 120° F. prior to its use in the immunoassay.

2. The lyophilized mixture as in claim 1 wherein said surfactant is octylphenoxypoly (ethylene oxy) ethanol.

3. The lyophilized mixture as in claim 1 wherein said mixture further comprises a polyvalent metal ion and a chelating agent.

4. The lyophilized mixture as in claim 1 wherein prior to lyophilization said mixture has a pH between about 7.2 and 7.6.

5. The lyophilized mixture as in claim 1 wherein said buffer salts comprise Hepes salt.

6. A diagnostic kit for carrying out an enzyme linked immunosorbent assay for detection of an antigen in a sample, said kit being suitable for home diagnostic application under ambient room temperature conditions and comprising the following separately contained components:
   (a) a solid support precoated with a first antibody and subsequently treated with a blocking solution comprising a mixture of a blocking agent and a water soluble sugar, said blocking agent being selected from the group consisting of bovine serum albumin, gelatin, milk protein and non-specific IgG antibody;
   (b) a vial of a lyophilized mixture comprising:
      (i) a conjugate of a second antibody and the enzyme peroxidase, said second antibody being of sufficient specificity to bind the enzyme to the antigen;
      (ii) buffer salts;
      (iii) a binding enhancing agent selected from the group consisting of polyethylene glycol, polyvinyl alcohol, polyvinyl pyrrolidone and dextran;
      (iv) a water soluble non ionic surfactant, said surfactant being present in the mixture in an amount sufficient to provide an appropriate amount of detergency for said immunoassay without having a deleterious effect on the conjugate;
      (v) a sugar selected from the group consisting of dextrin and trehalose, said sugar being present in the mixture in an amount sufficient to prevent discernible concentration gradients of the components in said mixture;
   said lyophilized mixture having the property of preserving the antibody reactivity and the immunologic binding specificity of the antibody-enzyme conjugate even if the mixture is exposed to temperatures between about 80° F. and 120° F. prior to its use in the immunoassay;
   (c) a measuring dispenser for the sample to be assayed;
   (d) a container comprising a solution of a buffer and a peroxide; and
   (e) a container comprising a solution of a chromogenic substrate of the enzyme peroxidase component of the conjugate of (b)(i) and a solvent;
said components being operable at a temperature between about 15° C. to less than 37° C.

7. The diagnostic kit as in claim 6 wherein said surfactant is octylphenoxypoly (ethyleneoxy) ethanol.

8. The diagnostic kit as in claim 6 wherein said separately contained components are operable at a temperature between about 15° C. to 28° C.

9. The diagnostic kit as in claim 6 wherein at least one of the first antibody or the second antibody is a monoclonal antibody.

10. An enzyme linked immunosorbent sandwich assay for detection of an antigen in a sample, said assay comprising the steps of:
   (a) coating a solid support with a first antibody against said antigen and incubating the coated solid support at a temperature between about 15° C. to less than 37° C. to adsorb the first antibody to the solid support;
   (b) treating the coated solid support with a blocking solution comprising a mixture of a blocking agent and a water soluble sugar, said blocking agent being selected from the group consisting of bovine serum albumin, gelatin, milk protein and non-specific IgG antibody;
   (c) preparing a liquid mixture comprising a sample solution to be tested for an antigen and a lyophilized mixture comprising:
      (i) a conjugate of a second antibody and the enzyme peroxidase, said second antibody being of sufficient specificity to bind the enzyme to the antigen;
      (ii) buffer salts;
      (iii) a binding enhancing agent selected from the group consisting of polyethylene glycol, polyvinyl alcohol, polyvinyl pyrrolidone and dextran;
      (iv) a water soluble non ionic surfactant, said surfactant being present in the mixture in an amount sufficient to provide an appropriate amount of detergency for said immunosorbent assay without having a deleterious effect on the conjugate; and
      (v) a sugar selected from the group consisting of dextrin and trehalose, said sugar being present in the mixture in an amount sufficient to prevent discernible concentration gradients of the components in said mixture;
   said lyophilized mixture having the property of preserving the antibody reactivity and the immunologic binding specificity of the antibody-enzyme conjugate even if the mixture is exposed to temperatures between about 80° F. and 120° F. prior to its use in the immunoassay;
   (d) incubating the coated solid support with said liquid mixture at a temperature between about 15° C. to less than 37° C., to permit any antigen in the sample to bind to the first antibody and to the second antibody of the conjugate to form an antibody-antigen complex in solid phase adsorbed to the solid support;

(e) separating materials adsorbed to the solid support from the unadsorbed materials; and (f) determining the presence of said enzyme in the adsorbed material by subjecting the adsorbed material to a chromogenic substrate and monitoring the visible color characteristics of said substrate.

11. The assay as in claim 10 wherein at least one of the first antibody or the second antibody is a monoclonal antibody.

12. The assay as in claim 10 wherein said lyophilized mixture further comprises a polyvalent metal ion and a chelating agent.

13. The assay as in claim 10 wherein said surfactant is octylphenoxypoly (ethylene oxy) ethanol.

14. The assay as in claim 10 wherein in step (d) said solid support is incubated with said liquid mixture at a temperature between about 15° C. to less than 28° C.

15. The assay as in claim 10 wherein in step (e) materials adsorbed to the solid support are separated from the unadsorbed materials by washing the solid support with water.

* * * * *